United States Patent
Douroumis et al.

(10) Patent No.: US 12,138,350 B2
(45) Date of Patent: *Nov. 12, 2024

(54) METHOD OF PRODUCING A EXTRUDED COMPOSITION

(71) Applicants: Cubic Pharmaceuticals Ltd., Kent (GB); Delta Pharmaceuticals Ltd., Kent (GB)

(72) Inventors: Dennis Douroumis, Kent (GB); Mohammed Maniruzzaman, Kent (GB); Saumil Kiritkumar Bhatt, Kent (GB); Anwar Ali, Kent (GB); Arun Jangra, Kent (GB)

(73) Assignees: Cubic Pharmaceuticals Ltd., Kent (GB); Delta Pharmaceuticals Ltd., Kent (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/549,900

(22) PCT Filed: Feb. 9, 2016

(86) PCT No.: PCT/GB2016/050294
§ 371 (c)(1),
(2) Date: Aug. 9, 2017

(87) PCT Pub. No.: WO2016/128727
PCT Pub. Date: Aug. 18, 2016

(65) Prior Publication Data
US 2018/0021263 A1    Jan. 25, 2018

(30) Foreign Application Priority Data

Feb. 9, 2015   (GB) .................. 1502077.9
Oct. 8, 2015   (GB) .................. 1517833.8

(51) Int. Cl.
| | |
|---|---|
| *A61K 9/20* | (2006.01) |
| *A61J 3/10* | (2006.01) |
| *A61K 9/14* | (2006.01) |
| *A61K 31/00* | (2006.01) |
| *A61K 31/192* | (2006.01) |
| *A61K 33/12* | (2006.01) |
| *A61K 47/32* | (2006.01) |
| *B29B 9/00* | (2006.01) |
| *B29C 48/00* | (2019.01) |
| *B29C 48/05* | (2019.01) |
| *B29B 9/06* | (2006.01) |

(52) U.S. Cl.
CPC ........... *A61K 9/2095* (2013.01); *A61J 3/10* (2013.01); *A61K 9/143* (2013.01); *A61K 9/20* (2013.01); *A61K 31/00* (2013.01); *A61K 31/192* (2013.01); *A61K 33/12* (2013.01); *A61K 47/32* (2013.01); *B29B 9/00* (2013.01); *B29C 48/0011* (2019.02); *B29C 48/05* (2019.02); *B29B 9/06* (2013.01)

(58) Field of Classification Search
None
See application file for complete search history.

(56) References Cited

U.S. PATENT DOCUMENTS

| | | | |
|---|---|---|---|
| 5,741,519 A | 4/1998 | Rosenberg et al. | |
| 6,322,816 B1 | 11/2001 | Zeidler et al. | |
| 6,376,481 B2 * | 4/2002 | Bruce ............... | A61K 9/0056 514/169 |
| 6,787,157 B1 | 9/2004 | Rosenberg et al. | |
| 2005/0129774 A1 | 6/2005 | Morein et al. | |
| 2009/0175940 A1 | 7/2009 | Gruber | |
| 2009/0302493 A1 | 12/2009 | Kessler et al. | |
| 2015/0164807 A1 | 6/2015 | Geissler et al. | |

FOREIGN PATENT DOCUMENTS

| | | |
|---|---|---|
| CA | 2352874 | 6/2000 |
| WO | WO 93/07859 | * 4/1993 |
| WO | WO-2011154009 | 12/2011 |
| WO | WO-2012056471 | 5/2012 |
| WO | WO-2014102745 | 7/2014 |

OTHER PUBLICATIONS

AEROSIL® 300 Product Information (Mar. 2013).*
Finch C.A. ((1987) Hydrophilic polymers. In: Dyson R.W. (eds) Specialty Polymers. Springer, Boston, MA).*
Shamma et al. (Powder Technology 237 (2013) 406-414).*
Crowley, M. et al., Pharmaceutical Applications of Hot-Melt Extrusion: Part 1, Drug Development and Industrial Pharmacy, 33(9): 909-926, 2007.
Gryczke, A. et al., Development and evaluation of orally disintegrating tablets (ODTs) containing Ibuprofen granules prepared by hot melt extrusion, Colloids and Surfaces B: Biointerfaces, 86: 275-284, 2011.
Thompson, M. et al., Twin screw granulation—review of current progress, Drug Development and Industrial Pharmacy, 41(8): 1223-1231, 2015.
Machine Translation of DE19855440.
Maclean et al., Manufacture and Performance Evaluation of Stable Amorphous Complex of an Acidic Drug Molecule and Neusilin, Journal of Pharmaceutical Sciences, 100(8): 3332-3344, Apr. 25, 2011.

(Continued)

*Primary Examiner* — Patricia Duffy
*Assistant Examiner* — Garen Gotfredson
(74) *Attorney, Agent, or Firm* — Julie K. Staple; Dinsmore & Shohl LLP

(57) ABSTRACT

The present invention relates to a method of producing a direct compression tablet composition comprising the step of processing ibuprofen, a hydrophilic polymer, and an inorganic excipient by an extrusion process to produce an extruded composition in which the ibuprofen forms a solid dispersion/solution within the hydrophilic polymer. The invention is particularly useful in preparing oral dissolvable tablets. Also provided are composition comprising an inorganic excipient and ibuprofen within a hydrophilic polymer.

17 Claims, 5 Drawing Sheets

(56) References Cited

OTHER PUBLICATIONS

Maniruzzaman, M. et al., Continuous twin-screw granulation for enhancing dissolution of poorly water soluble drug, International Journal of Pharmaceutics, 496: 52-62, Sep. 18, 2015.

Maniruzzaman, M et al., Poster No. W5235, Neusilin@-Polymer Extrudates for the Developments of Solid Dispersions, Final Program and Exhibit Guide, 2013 AAPS Annual Meeting and Exposition, Nov. 10-14, 2013.

Communication pursuant to Rule 114(2) EPC, European Patent Application No. 16709488.7, Jun. 1, 2021.

Communication pursuant to Rule 114(2) EPC, European Patent Application No. 16709489.5, Jun. 1, 2021.

Maniruzzaman, M. et al., One-step continuous extrusion process for the manufacturing of solid dispersions, International Journal of Pharmaceutics, 496: 42-51, 2015.

\* cited by examiner

METHOD OF PRODUCING A EXTRUDED COMPOSITION

FIELD OF THE INVENTION

The invention relates inter alia to an improved method of producing an extruded composition comprising ibuprofen as well as pharmaceutical compositions, such as direct compression tablet compositions, comprising the same.

BACKGROUND TO THE INVENTION

Hot-melt extrusion (HME) has been used in a wide range of manufacturing processes. Aside from its use in the plastics, rubber and food manufacturing sectors, HME has been used in the manufacture of pharmaceutical dosage forms e.g. tablets or films. In general terms, HME involves pumping a mixture of raw materials at controlled (often elevated) temperature and/or pressure through a barrel to produce a composition that is forced out of the barrel through a die. The raw materials are typically fed into the extruder (the extruder barrel) via a hopper. Flow through the barrel is usually associated with mixing, grinding, compressing, kneading and/or venting. Within the barrel are typically one or two rotating screws (corotating or counter rotating).

Initial extruded compositions (extrudates) usually require further processing before final use, for example into powders for tabletisation in the field of pharmaceuticals. However, many prior art extrusion methods, especially where ibuprofen is extruded, result in sticky extrudates that require cryo-milling for powder formation. Cryo-milling is a time consuming and costly processing step that inhibits the scale-up of such processes to an industrial operation.

It is amongst the objects of the present invention to attempt a solution to this problem, and to improve various characteristics of ibuprofen extrudates (and pharmaceutical forms derived therefrom) for pharmaceutical use, such as improved drug-loading, stability and taste-masking and, in the case of tablet forms in particular, increased disintegration rate, increased hardness and decreased friability.

SUMMARY OF THE INVENTION

Accordingly, the invention provides a method of producing a direct compression tablet composition comprising ibuprofen, said method comprising the steps of:
(a) providing ibuprofen;
(b) providing a hydrophilic polymer;
(c) providing an inorganic excipient;
(d) processing (a) to (c) by an extrusion process to produce an extruded composition wherein the ibuprofen forms a solid dispersion/solution within the hydrophilic polymer;
(e) blending the extruded composition with one more pharmaceutically acceptable excipients to produce a composition blend; and
(f) directly compressing the composition blend into a direct compression tablet.

In one embodiment, the extruded composition comprises ibuprofen in an amount less than equal to 60 wt %, less than or equal to 50 wt %, less than or equal to 40 wt %.

In one embodiment, the extrusion process is a hot melt extrusion (HME) process.

In preferred embodiments, the extruded composition is in the form of a strand and/or the method further comprises cutting the extruded strands into pellets (preferably wherein the method further comprises micronization of the pellets to form granules).

In preferred embodiments, the inorganic excipient has a specific surface area of more than 1.00 $m^2/g$ and/or a Carr Index of less than 18. Preferably the inorganic excipient is selected from the group consisting of:
A magnesium phosphate
An iron pyrophosphate (preferably ferric)
An iron orthophosphates (preferably ferric)
A sodium phosphate
A potassium phosphate
A calcium phosphate
Silicon dioxide
Magnesium Stearate
Tricalciumphophate
Silica
Hydrated Silica
Alumina Magnesium Metasilicate
Aluminum Calcium Sodium Silicate
An aluminium silicate
An iron silicate In one embodiment, the inorganic excipient is a metal aluminosilicate.

The most preferred inorganic excipients are:
Magnesium Alumino-metasilicate ($Al_2O_3 \cdot MgO \cdot 1.7SiO2 \cdot xH2O$)
SiO2
Dibasic Calcium Phosphate Anhydrous (DCPA)-($CaHPO_4$)

Also provided is a direct compression tablet composition obtainable by any of the above methods.

Provided is a direct compression tablet composition comprising:
(a) An inorganic excipient; and
(b) Ibuprofen in solid dispersion/solution within a hydrophilic polymer.

Preferably, said composition is in the form of a strand, pellets or a powder. In preferred embodiments, the inorganic excipient is as defined above with respect to the provided methods.

In one embodiment, the tablet is an oral-dissolvable tablet (ODT). For example, the tablet is a quick-melt tablet.

Included within the scope of the invention is a method of producing an extruded composition, a composition and a tablet substantially as described herein.

BRIEF DESCRIPTION OF FIGURES

The following is a brief description of the figures.

DETAILED DESCRIPTION OF THE INVENTION

Figure 1A:
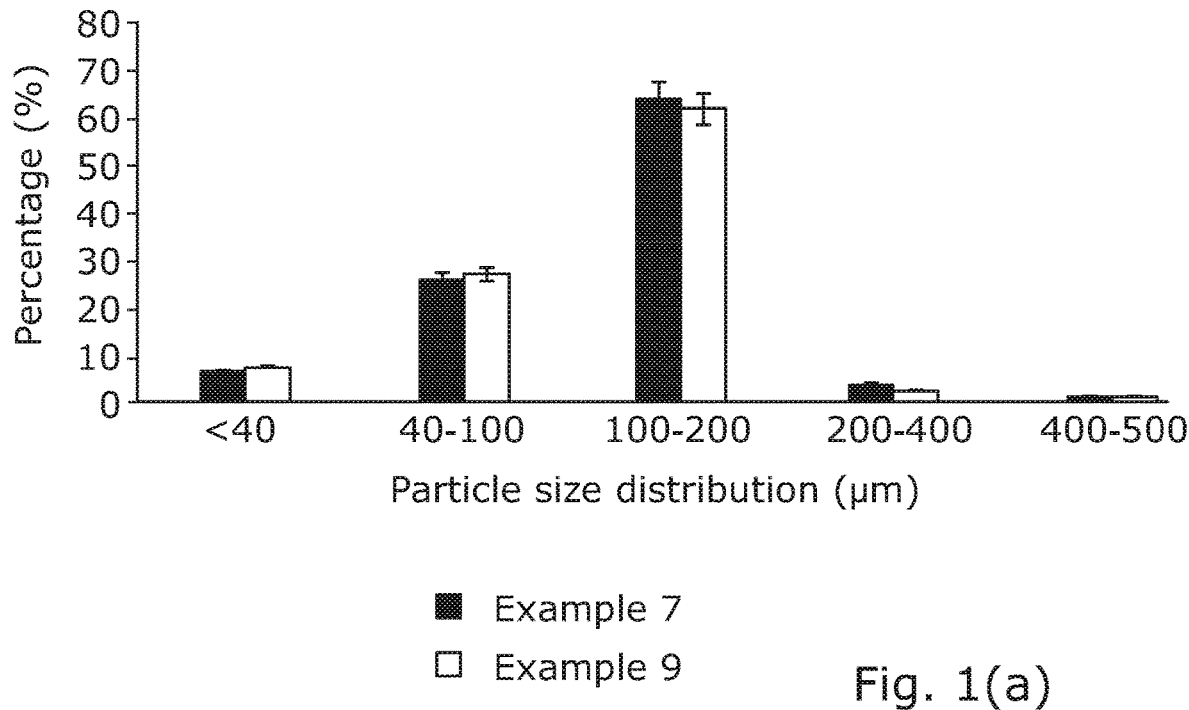
FIGS. 1a and 1b show the particle size distributions of Example 3, 7, 9 and 11.

The invention relates to a method of producing an extruded composition comprising ibuprofen: (RS)-2-(4-(2-methylpropyl)phenyl)propanoic acid. Ibuprofen can be in the form of a racemate or either of the S- or R-enantiomer. The acid and pharmaceutical salt forms are contemplated. Ibuprofen is preferably present in the extrudate and/or pharmaceutical forms thereof at at least 10% w/w, such as 10-60% w/w, more preferably 20-50% w/w, such as, for the extrudates, at least 35% w/w, preferably 35-45% w/w (e.g. 40% w/w) and, for the pharmaceutical forms, at least 25% w/w, preferably 25-35% w/w (e.g. 30% w/w).

In one embodiment, the extruded composition comprises ibuprofen in an amount of less than or equal to 60 wt %, less than or equal to 50 wt %, or less than or equal to 40 wt %, based on the total weight of the extruded composition.

In preferred aspects of all embodiments, the ibuprofen is amorphous ibuprofen.

In the claimed method a hydrophilic polymer is provided (e.g. a pharmaceutically-acceptable hydrophilic polymer). Suitable polymers will be those that are suitable for melt extrusion, i.e. they will have a melting temperature (technically, a glass transition temperature—$T_G$) that is below the temperatures used for extrusion, e.g. below 150° C. preferably below 120° C., and more preferably below 100° C. A polymer should be chosen that has a $T_G$ low enough so as not to cause degradation of the ibuprofen when melted (i.e. at, or slightly above, the $T_G$). Ibuprofen is reported to be stable up to about 152° C. (Ramukutty and Ramachandran, Journal of Crystallization Process and Technology, 2014, 4, 71-78, "Reaction Rate Models for the Thermal Decomposition of Ibuprofen Crystals"), hence the preferred upper limit on $T_G$ of 150° C.

Suitable polymers should also be hydrophilic, and may be either neutral or have pH-dependent solubility.

Within the range of suitable polymers, the following polymers are specifically envisaged:
- polyvinyl caprolactam-polyvinyl acetate-polyethylene glycol graft copolymer such as that sold under the Registered Trademark Soluplus, and having a $T_G$ of ca. 70° C.
- vinylpyrrolidone-vinyl acetate copolymers (See monograph "Copovidone" and the JPE monograph, "Copolyvidone") such as that sold under the Registered Trademark Kollidon, and having $T_G$ of ca, 101° C.
- copolymer based on dimethylaminoethyl methacrylate, butyl methacrylate, and methyl methacrylate such as that sole under the Registered Trade Mark EPO, and having a $T_G$ of ca. 45° C.
- anionic copolymer based on methacrylic acid and ethyl acrylate
- N-vinyl-2-pyrrolidone and vinyl acetate copolymer such as that sold under the Registered Trademark Plasdone S630, and having a $T_G$ of ca. 109-112° C.

In the claimed method an inorganic excipient is provided (e.g. a pharmaceutically-acceptable inorganic excipient).

In one embodiment, the extruded composition comprises the inorganic excipient in an amount greater than equal to 10 wt %, greater than equal to 15 wt %, or greater than equal to 20 wt %, In the present invention, the inorganic excipient is used as a drug carrier. Notably in the present invention, the inorganic excipient is not merely employed as a lubricant in order to improve the formulation process.

In particular, the inorganic excipient should preferably have the following features:

Heat Stability: The inorganic excipient should be heat-stable at the temperatures used for the process. As ibuprofen degrades above approximately 152° C., the inorganic excipient should be stable to at least this temperature. Most inorganic excipients are heat-stable to a much higher degree.

Physical Form: The inorganic excipient should be in a powder or granular form. Particles should preferably have a particle size of less than about 500 microns, for example in the range of about 40-500 microns.

Specific Surface Area: The inorganic excipient should have a high, specific surface area (SSA) to allow interaction with other components in the composition. Preferably, the SSA should be at least 100 $m^2/g$, or at least 300 $m^2/g$, or at least 300 $m^2/g$, or at least 500 $m^2/g$ or at least 800 $m^2/g$. Excipients having an SSA of between 100-800 $m^2/g$, such as between 200-300 $m^2/g$, are particularly preferred.

Loss on Drying: The inorganic excipient should exhibit low loss on drying, and should lose less than 20%, preferably less than 15%, or 10%, or 5%, or 2%, or most preferably less than 1% weight on drying at 110° C. for 7 hr.

Angle of Repose: To give good handling properties, excipients having an angle of repose of between 25°-45° are particularly preferred.

Flowability: The inorganic excipient should exhibit good flow properties. This may be measured using the Carr Index (a measurement known in the pharmaceutical industry for measurement of compressibility and flowability). An excipient having a Carr Index of less than 18, or less than 17 or 16 is preferred. Particularly preferred are excipients having a Carr Index of less than 15, for example between 5-15.

The following inorganic excipients are envisaged as being appropriate for use:
- Magnesium phosphates
- Ferric pyrophosphates and orthophosphates
- Sodium phosphates
- Potassium phosphates
- Calcium phosphates
- Magnesium stearate
- Tricalciumphosphate
- Silica, Hydrated Silica, Alumina Magnesium Metasilicate Alumina Magnesium Metasilicate, Aluminum Calcium Sodium Silicate, Aluminum and Iron Silicates A preferred inorganic excipient is a metal aluminosilicate. Particularly preferred excipients are the amorphous form of Magnesium Alumino-metasilicate ($Al_2O_3 \cdot MgO \cdot 1.7SiO_2 \cdot xH_2O$), $SiO_2$ and dibasic calcium phosphate anhydrous ($CaHPO_4$), commonly known as DCPA.

Once the ibuprofen, hydrophilic polymer and inorganic excipient, are provided, they are preferably mixed (e.g. to homogeneity) before being subjected to an extrusion process, whereby the components are passed along a barrel and out of the barrel via a die. In the claimed method this extrusion leads to an extruded composition wherein the ibuprofen forms a solid dispersion/solution within the hydrophilic polymer. The skilled person will be able to select appropriate processing parameters once the particular ingredients and extruder apparatus have been chosen. Preferably, the extrusion process is carried out at less than 140° C. (e.g. 70° C. to 130° C., such as 120° C.). In experimental work, a Eurolab 16 mm Thermo-Fisher extruder was used, with a screw speed rate of 50 to 400 rpm (e.g. 50-100 rpm) and a feed rate of 0.5 kg/hr to 5 kg/hr (e.g. 1.5 kg/hr). Preferably, a twin screw extruder is used. The process may be scaled up for larger scale production by routine experimentation and industry scale-up methodologies.

In the present invention, a solid dispersion/solution refers to a solid dispersion or a solid solution. A solid dispersion is generally a mixture of two or more components where one component is a drug molecule, e.g. ibuprofen, dispersed onto the matrices of other components. For example, the term "solid dispersion" may be defined as a drug molecule, e.g. ibuprofen, in a solid matrix. The solid matrix may be a polymer. The dispersed state may have many forms such as eutectic mixtures, crystalline/glass solutions, amorphous/crystalline suspensions and solid solutions. In a preferred embodiment, the dispersed state is a solid solution. In one embodiment, the solid dispersion may be a dispersion of ibuprofen in an amorphous polymer matrix, wherein the ibuprofen is preferably in the molecularly dispersed state.

By solid solution, it is meant e.g. that the ibuprofen is intimately mixed at a molecular scale with the polymer. The formation of a solid solution, rather than merely a mixture of solids may be determined by the use of differential scanning calorimetry (DSC) in which the normal melting peak of ibuprofen disappears, or is at least significantly reduced, when the ibuprofen is in solid solution, rather than merely a mixture (see Gryczke, A. et al, Colloids and Surfaces B: Biointerfaces 86(2001) 275-284, for details of such a technique). In preferred compositions, at least 90% w/w of the ibuprofen is in the form of a solid solution, and preferably at least 95% w/w, and more preferably at least 98% w/w.

In one embodiment, the method further comprises cutting the extrudate into pellets. Furthermore, the method may further comprise micronization of the pellets. For example, micronization of the pellets could form granules and/or a powder.

In preferred embodiments the die of the barrel is configured to produce a strand of extrudate (e.g. rod-shaped). Preferably, the extrudate is further processed via cutting into pellets of e.g. 1 cm or less (e.g. 1 mm) in length, for example using an online pelletizer. In preferred embodiments, these pellets are then processed into a powder via micronisation (e.g. using a cutter mill). By powder, it is meant e.g. that the material is in the form of fine, discrete particles. Such a powder will typically have an average particle size of less than about 1 mm diameter (i.e. will pass through a 1mn mesh), and preferably less than about 600 μm, or less than about 500 μm, or less than about 300 μm, or less than about 100 μm. Particularly preferred powders are those having a mean particle size of about 350 μm, e.g. a powder in which at least 90% (w/w) of the particles have a particle size of between 1.50 μm and 550 μm.

In the claimed method the produced extrudates are non-sticky and hence can be processed into a powder without the need for cryo-milling. (And in preferred embodiments, therefore, the claimed method does not comprise a cryo-milling step.) This increases the throughput of the production method (by reducing processing times). In preferred embodiments, an anti-tacking agent e.g. talc is not used in the production method (and e.g. such an anti-tacking agent is present in the composition of the invention at less than 10% w/w, preferably less than 5% w/w, preferably less than 1% w/w, preferably less than 0.1% w/w, and is most preferably absent).

The compositions of the invention can be incorporated into pharmaceutical forms for administration of the ibuprofen to an individual in need thereof, such as solid forms (e.g. tablets and films and the like). A particular form of interest is a tablet, for e.g. oral-enteral delivery. In particularly preferred embodiments the claimed tablet is an orally-dissolvable tablet (ODT), a tablet configured to disintegrate and/or dissolve in the mouth (e.g. on or under the tongue), for instance upon contact with saliva, prior to swallowing. Advantages of an ODT formulation include increased compliance (especially in individuals with dysphagia) and more rapid ibuprofen absorption.

In preferred embodiments, the claimed tablet has a hardness of 5 kilopond (Kp) or more, preferably 8 Kp or more, and/or a friability of 1% or less, preferably 0.8% or less, more preferably 0.6% or less, and/or an in vivo disintegration time (as measured by the protocol herein) of 30 s or less, preferably 20 s or less, more preferably 15 s or less, most preferably 10 s or less, and/or an in vitro disintegration time (as measured by the protocol herein) of 25 s or less or 20 s or less, preferably 15 s or less, more preferably 10 s or less, most preferably 5 s or less.

The tablets/ODTs of the present invention show comparable or improved characteristics compared with prior art products in terms of ibuprofen loading, taste-masking and stability, and tablet hardness, friability and disintegration time.

In particular, the tablets of the invention provide a rare combination of favourable disintegration in the mouth and favourable hardness. For example, the tablet of the present invention are robust, i.e. not brittle, which has huge advantages in the context of packaging the tablets. Typically, the tablets of the present invention exhibit levels of weight loss in packaging as low as 0.1-0.2 wt %. This is considerably less than some conventional tablets.

Other aspects of the invention include, but are not limited to the following.

There is provided a method of producing an extruded composition comprising ibuprofen, said method comprising the steps of:
(a) providing ibuprofen;
(b) providing a hydrophilic polymer;
(c) providing an inorganic excipient; and
(d) processing (a) to (c) by an extrusion process to produce an extruded composition wherein the ibuprofen forms a solid solution within the hydrophilic polymer.

There is provided a composition obtainable by the method described above.

There is provided a composition comprising:
(a) an inorganic excipient; and
(b) ibuprofen in solid solution within a hydrophilic polymer.

There is provided a tablet comprising an extruded composition as described above.

In one embodiment, the tablet is a oral-dissolvable tablet (ODT).

Please note that wherever the term 'comprising' is used herein we also contemplate options wherein the terms 'consisting of' or 'consisting essentially of' are used instead.

EXAMPLES

Figure 1B:
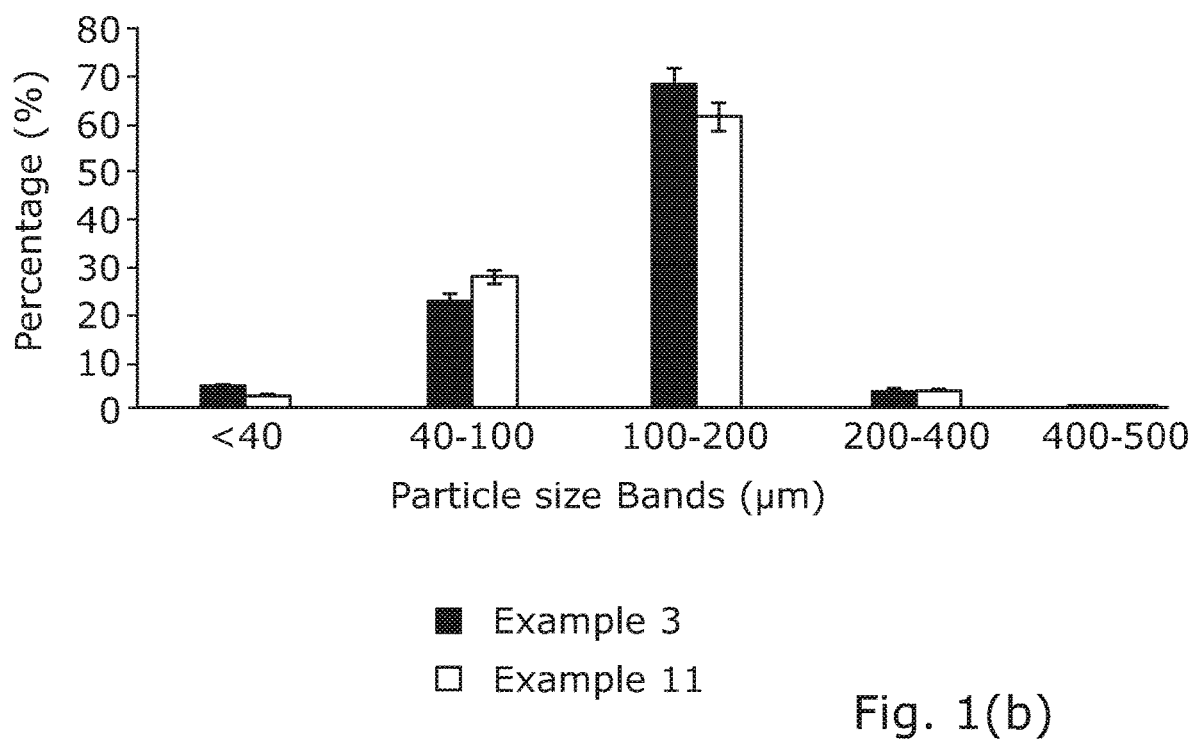

For each Example extrusion, ibuprofen (base, racemate) powder was mixed thoroughly with hydrophilic polymer and inorganic excipient for 10 min using a turbula TF2 mixer (Basel, Switzerland) to form a homogeneous powder prior to hot-melt extrusion (HME) processing. In all examples, powder blends were extruded at temperatures of 120° C. using a screw speed of 50 to 100 rpm with a feed rate of 1.5 kg/h. In all cases a EuroLab 16 twin screw extruder (ThermoFisher, Germany) was used. The EuroLab 16 was connected to a terminal PC and all processing parameters controlled via the appropriate software supplied by Thermo Fisher. Extrudates were collected as rod-shaped strands with uniform drug distribution and relatively high drug loading (40% w/w of ibuprofen). The extrudates were non-sticky and hence could be, and were, cut into pellets of 1 mm length using an online pelletizer (ThermoFisher, Germany) The pellets were subsequently micronized using a cutter mill (Retsch, Germany). FIGS. 1b and 1b show the particle size distribution of Examples 3, 7 9 and 11 after micronization. In particular, FIG. 1(a) shows the particle size distribution of Example 7 and Example 9. FIG. 1(b) shows the particle size distribution of Example 3 and Example 11. Particle size distributions were similar for all examples listed.

ODT batches were then prepared using batch sizes of 100 g. All powdered extrudates were passed through a mesh sieve with an aperture of 500 μm before use. The batches were blended with sodium stearyl fumarate (1%) or magnesium stearate/silicon dioxide (0.8%/0.2%) in a Turbula TF2 mixer (Basel, Switzerland) for 10 minutes. Routine experimentation can be used to determine appropriate mixing regimes for particular formulations used, or where the process is scaled up. Blends were directly compressed on a Flexitab Inlayer tablet press (Oystar-Manesty, Germany) using 13 mm normal flat punches. Dwell time was set at 30 ms and the compaction three varied from 8-12 kN to obtain tablets of about 3 mm thickness (average weight 600 to 630 mg), ODTs were further evaluated to characterise their properties. Please note that all prepared ODTs were stable under ICH storage conditions (e.g. 40° C. and 75% relative humidity for 6 months) and showed effective taste masking. The ODTs showed particularly high hardness, low friability and rapid disintegration times. Results from these tests are shown at the bottom of the results table.

All prepared tablets were evaluated for the uniformity of thickness, hardness (Erweka TBH 28, Frankfurt, Germany), friability (Erweka friabilator, model A3R, Frankfurt, Germany), and in vitro disintegration time.

In vitro disintegration time was measured for 6 tablets by inserting disks using 900 ml purified water at 37±2° C. in Disintegration Apparatus (Erweka, model ZT4, Heusenstamm, Germany) according to USP 27 NE 22 test. (United States Pharmacopoeia, National Formulary).

In vivo disintegration was performed by a panel of 6 healthy human volunteers from whom written consent was first obtained. The study is in accordance to the Code of Ethics of the World Medical Association (Declaration of Helsinki). The healthy volunteers of either sex (age 18-25) were selected, trained and the one tablet was held in the mouth after rinsing and the time required for complete disintegration of the tablet was recorded. The time when the tablet placed on the tongue disintegrated without leaving any lumps was taken as the end point.

Results

In the following results table:
All values are % w/w
Hashed areas are described by the later table of chemical designation of trade names
MCC=microcrystalline cellulose
MAS=amorphous form of Magnesium Alumino-metasilicate ($Al_2O_3 \cdot MgO \cdot 1.7SiO_2 \cdot xH_2O$)
MgSt=magnesium stearate
SSF=sodium stearyl fumarate (e.g. as sold under the RTM "PRUV")
DT=disintegration time; +/−1 s in all cases
Hardness+/−0.5 Kp in all cases

| | Chemical entity | Trade name | Ex. 1 | Ex. 2 | Ex. 3 | Ex. 4 | Ex. 5 | Ex. 6 |
|---|---|---|---|---|---|---|---|---|
| Extrudate Composition | Ibuprofen | — | 40 | 40 | 40 | 40 | 40 | 40 |
| | | Soluplus | 35 | 30 | — | — | 35 | — |
| | | Kollidon VA64 | — | — | 35 | 30 | — | — |
| | | EPO | — | — | — | — | — | — |
| | | Plasdone S630 | — | — | — | — | — | 30 |
| | MAS | — | 25 | 30 | 25 | 30 | — | — |
| | DCPA | — | — | — | — | — | 25 | 30 |
| Tablet Composition | Extrudate from above | | 71.4 | 71.4 | 71.4 | 71.4 | 71.4 | 79.11 |
| | Sorbitol | — | — | — | — | — | 12.6 | — |
| | Mannitol | Pearlitol | 6.1 | — | 7 | 7.6 | — | — |
| | MCC | — | 6.5 | 7.6 | 10.6 | — | — | — |
| | | XL 10 | — | — | — | — | — | — |
| | | XL | 15 | 20 | 10 | 20 | 15 | — |
| | | Vivasol | — | — | — | — | — | 19.88 |
| | | Kollidon CL-SF | — | — | — | — | — | — |
| | | Kollidon CL-MF | — | — | — | — | — | — |
| | SSF | PRUV | 1 | 1 | 1 | 1 | 1 | 1 |
| Results | Hardness (Kp) | | 9.6 | 10.6 | 11.6 | 10.6 | 8.6 | 10.6 |
| | Friability (%) | | 0.9 | 0.8 | 0.7 | 0.9 | 1.0 | 0.9 |
| | In vivo DT (s) | | 21 | 19 | 29 | 29 | 32 | 20 |
| | In vitro DT (s) | | 16 | 12 | 22 | 20 | 24 | 12 |

-continued

| | Chemical entity | Trade name | Ex. 7 | Ex. 8 | Ex. 9 | Ex. 10 | Ex. 11 |
|---|---|---|---|---|---|---|---|
| Extrudate Composition | Ibuprofen | — | 40 | 40 | 40 | 40 | 40 |
| | | Soluplus | — | — | — | — | — |
| | | Kollidon VA64 | — | — | — | — | — |
| | | EPO | 40 | 30 | 20 | 20 | 15 |
| | | Plasdone S630 | — | — | — | — | — |
| | MAS | — | 20 | 30 | 40 | 40 | 45 |
| Tablet Composition | Extrudate from above | | 71.4 | 71.4 | 71.4 | 71.4 | 71.4 |
| | Sorbitol | — | — | — | — | — | — |
| | Mannitol | Pearlitol | 6.1 | — | 7 | 7.6 | 12.6 |
| | MCC | — | 6.5 | 7.6 | 10.6 | — | — |
| | | XL 10 | 15 | — | — | 20 | — |
| | | XL | — | — | — | — | — |
| | | Vivasol | — | 20 | — | — | — |
| | | Kollidon CL-SF | — | — | 10 | — | — |
| | | Kollidon CL-MF | — | — | — | — | 15 |
| | SSF | PRUV | — | 1 | 1 | 1 | 1 |
| | MgSt | — | 0.8 | — | — | — | — |
| | SiO$_2$ | — | 0.2 | — | — | — | — |
| Results | Hardness (Kp) | | 8.6 | 8.9 | 9.6 | 10.6 | 9.6 |
| | Friability (%) | | 0.6 | 0.8 | 0.8 | 0.7 | 0.8 |
| | In vivo DT (s) | | 15 | 21 | 8 | 19 | 20 |
| | In vitro DT (s) | | 9 | 13 | 4 | 12 | 13 |

Table of Chemical Designation of Trade Names

| Trade name | Chemical Designation |
|---|---|
| Soluplus | Polyvinyl caprolactam-polyvinyl acetate-polyethylene glycol graft copolymer (PCL-PVAc-PEG)) |
| Kollidon VA64 | Vinylpyrrolidone-vinyl acetate copolymers |
| EPO | Dimethylaminoethyl methacrylate, butyl methacrylate, and methyl methacrylate copolymer |
| Plasdone S630 | N-vinyl-2-pyrrolidone and vinyl acetate copolymer |
| XI 10 | Polyplasdone crossprovidone superdisintegrants |
| XI | Polyplasdone crossprovidone superdisintegrants |
| Vivasol | Croscarmellose sodium |
| Kollidon Cl-SF | Crospovidone CL-SF |
| Kollidon Cl-MF | Crospovidone CL-MF |

In vivo taste masking evaluation was also performed on 6 healthy human volunteers from whom informed consent was first obtained. The study was in accordance to the Code of Ethics of the World Medical Association (Declaration of Helsinki). The healthy volunteers of either sex (3 males and 3 females, age 18-25) were selected, trained and the extruded granules were evaluated (no exclusion criteria). The equivalent of 200 mg of pure IBU extrudates (containing equal amounts of IBU) were held in the mouth for 60 seconds and then spat out. The selection of samples was random and in between of two samples analysis mineral water was used to wash each volunteer's mouth. The bitterness was recorded immediately according to the bitterness intensity scale from 0 to 5 where 0, 1, 2, 3, 4 and 5 indicate none, threshold, slight, moderate, bitter and strong bitterness.

Figure 2:
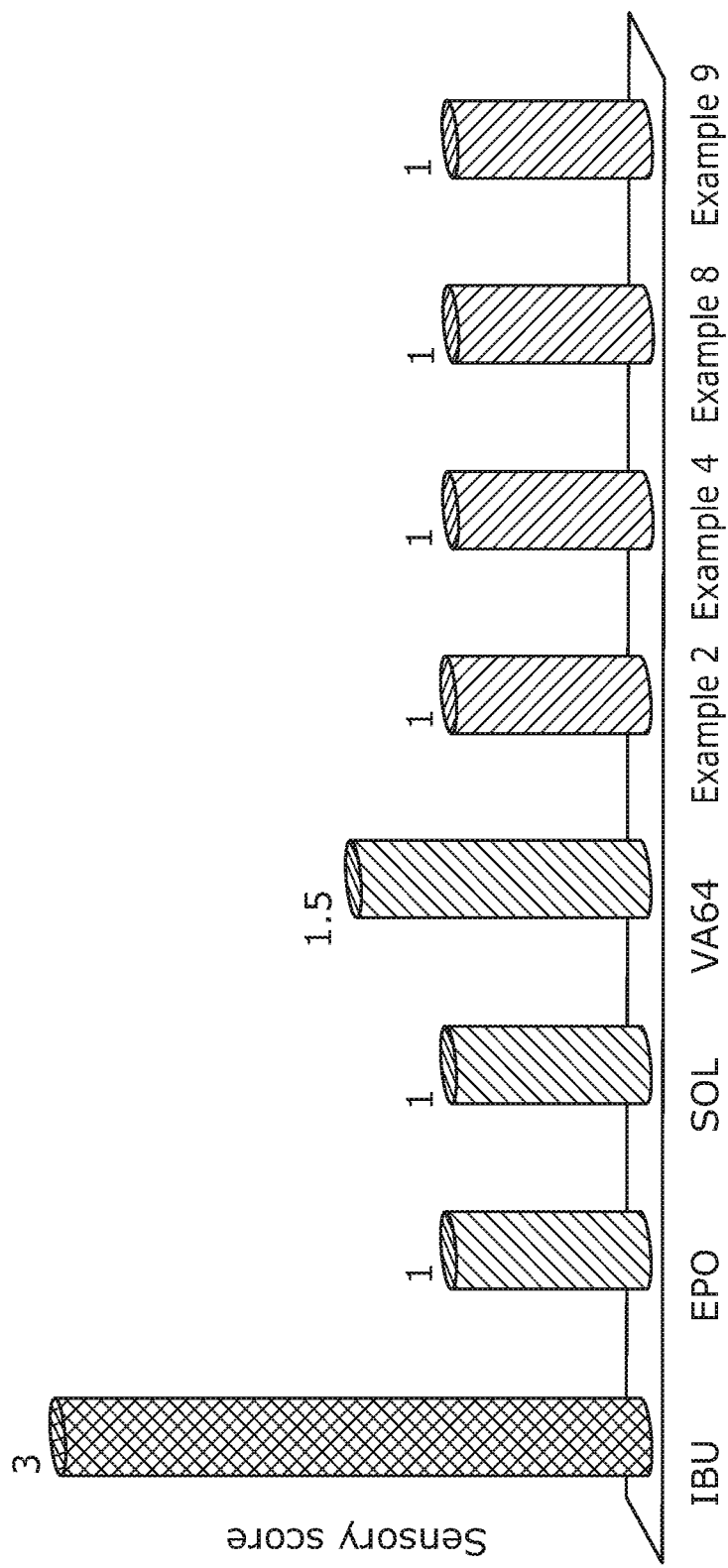
FIG. 2 shows the results of a taste masking evaluation for a range of example formulations and pure ibuprofen.

FIG. 2 and Table 2 show the results of the taste masking evaluation for a range of the example formulations.

TABLE 2

Results of Taste Masking Evaluation

| Formulation | Sensory Score |
|---|---|
| Ibuprofen | 3 |
| EPO | 1 |
| Soluplus | 1 |
| Kollidon VA64 | 1.5 |
| Example 2 | 1 |
| Example 4 | 1 |
| Example 8 | 1 |
| Example 9 | 1 |

FIG. 2 and Table 2 show that, in all cases, the bitter taste of ibuprofen was successfully masked. For the pure ibuprofen extrudates, a mean bitterness intensity of 3.0 was recorded. For all of the other examples tested, a mean bitterness intensity of 1.0 was recorded, except for the example containing the polymer Kollidon VA64, for which a mean bitterness intensity of 1.5 was recorded. It can be seen that all of the formulations were successful at masking the bitterness of ibuprofen.

Figure 3:
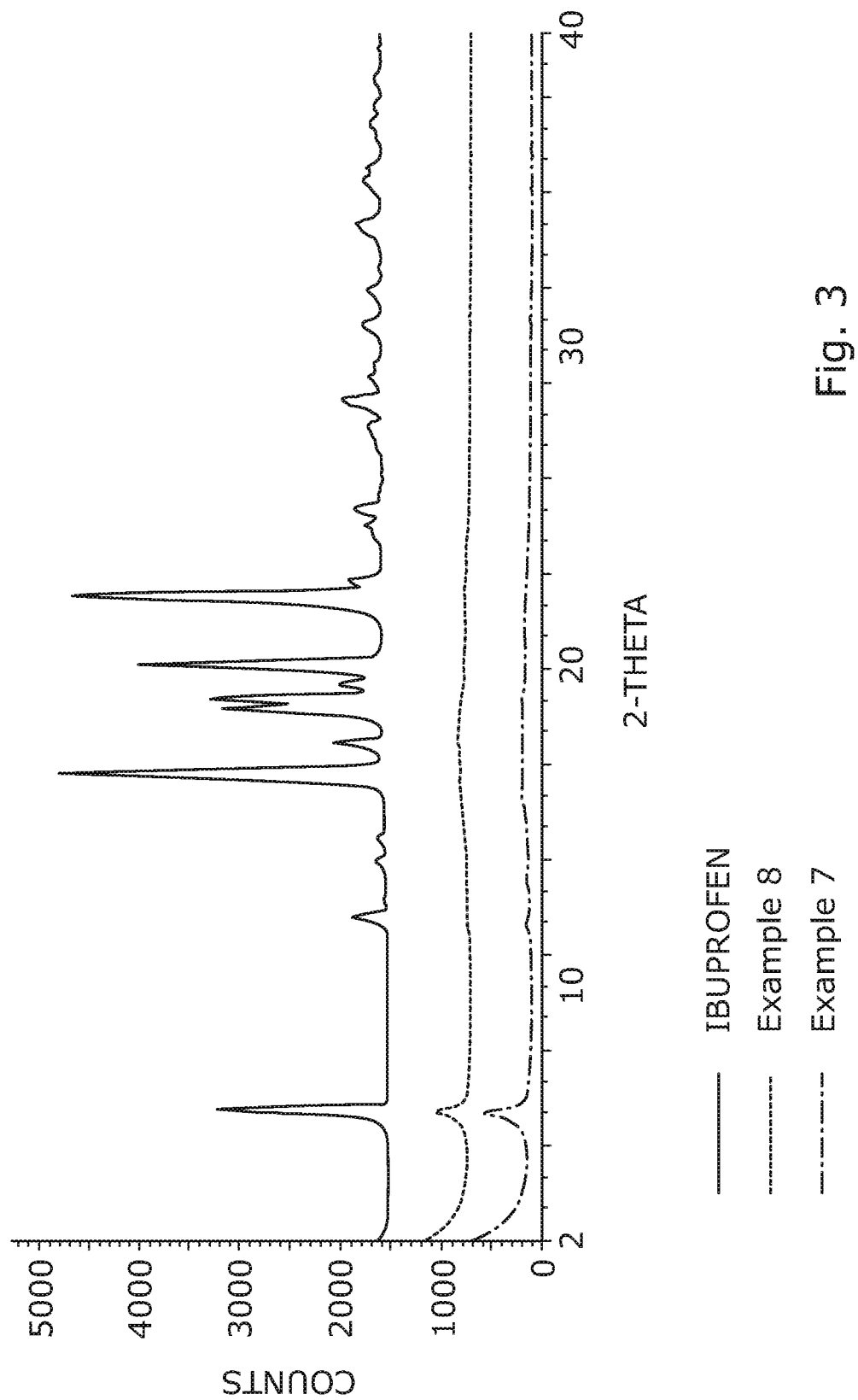
FIG. 3 shows XRPD diffractograms of pure ibuprofen, Example 7 and Example 8.

The extrudates produced by the claimed process were examined by X-Ray Powder Diffraction (XRPD), to determine the state of the ibuprofen in the products. It is known that amorphous forms of compounds generally exhibit higher dissolution rates than their crystalline counterparts. FIG. 3 shows XRPD diffractograms of pure ibuprofen, and two of tire example processed extrudates (Example 7 and 8). The top trace shows the characteristic XRPD response of crystalline ibuprofen, the collection of peaks at 2-theta angles from about 16° to about 24° being good indicators of crystallinity. The peak at the 2-theta angle of approximately 6° is known to be also present in amorphous ibuprofen, and is likely to be due to the molecular structure of the compound rather than its higher order crystalline structure.

The middle trace represents Example 8, The bottom trace represents Example 7. Corresponding traces for the extrudates of Examples 7 and 8 show virtually none of the crystallinity of the pure ibuprofen. In all samples, the degree of remaining crystallinity was determined (by analysis of the XRPD data) to be less than 15%, and in most cases, significantly lower than this, for example <10, <5% and even <2%.

Figure 4:
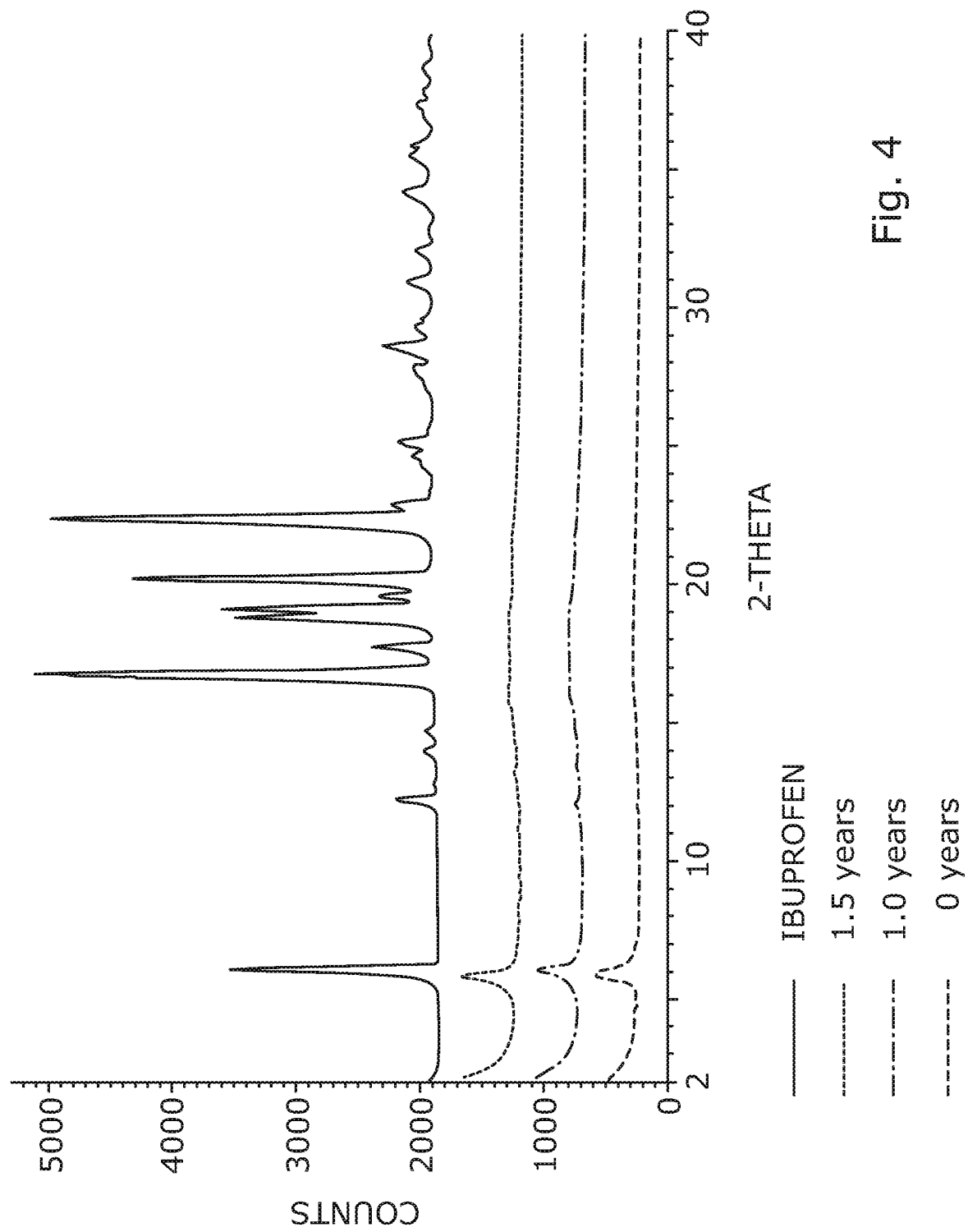
FIG. 4 shows XRPD diffractograms relating to pure ibuprofen and Example 9 at 0 years, 1.0 years and 1.5 years representing a stability test conducted in relation to Example 9.

Samples of the extrudates were also tested for stability. A sample was kept at ambient conditions for a period of 1.5 years, and periodically subjected to XRPD analysis as above. Results for such a stability test on Example 9 are shown in the diffractogram of FIG. 4. The top trace represents ibuprofen. The trace immediately below represents the results after 1.5 years. The trace immediately below this represents the results after 1.0 years. The bottom trace represents the results after 0 years. As for the examples shown in FIG. 3, Example 9 showed effectively no crystallinity immediately after manufacture (0 years curve). The sample was re-tested after 1 and 1.5 years, and again no crystallinity was evident, demonstrating the long-term stability of the compositions. It should also be noted that for stability of final product, the extrudates would normally be incorporated, into a tablet, as described herein, and that tableting is known to increase the stability of API formulations incorporated into them.

In vitro dissolution studies were also carried out at pH 1.2 on the example products, and compared to a commercially available ibuprofen formulation sold under the Registered Trademark Nurofen Meltlets.

In vitro dissolution studies were carried out in 900 ml of 0.1 M hydrochloric acid with a pH 1.2 for 2 hr using a Varian 705 DS dissolution paddle apparatus USP II (Varian Inc. North Carolina, US) at 100 rpm and 37±0.5° C. At predetermined time intervals samples were withdrawn for HPLC assay. All dissolution studies were performed in triplicate.

The amount of ibuprofen released from tablets was determined by HPLC. An Agilent Technologies system equipped with a HICROM S50DS2, 5 μm×150 mm×4 mm in column at 214 nm was used for the IBU HPLC assay. The mobile phase consisted of acetonitrile/water (1% acetic acid) (65:35:0.1, v/v). The flow rate was set at 1.5 ml/min. The IBU calibration curves was constructed using a concentrations range varying from 10 μg/ml to 50 μg/ml with 20 μl injection volume.

Figure 5:
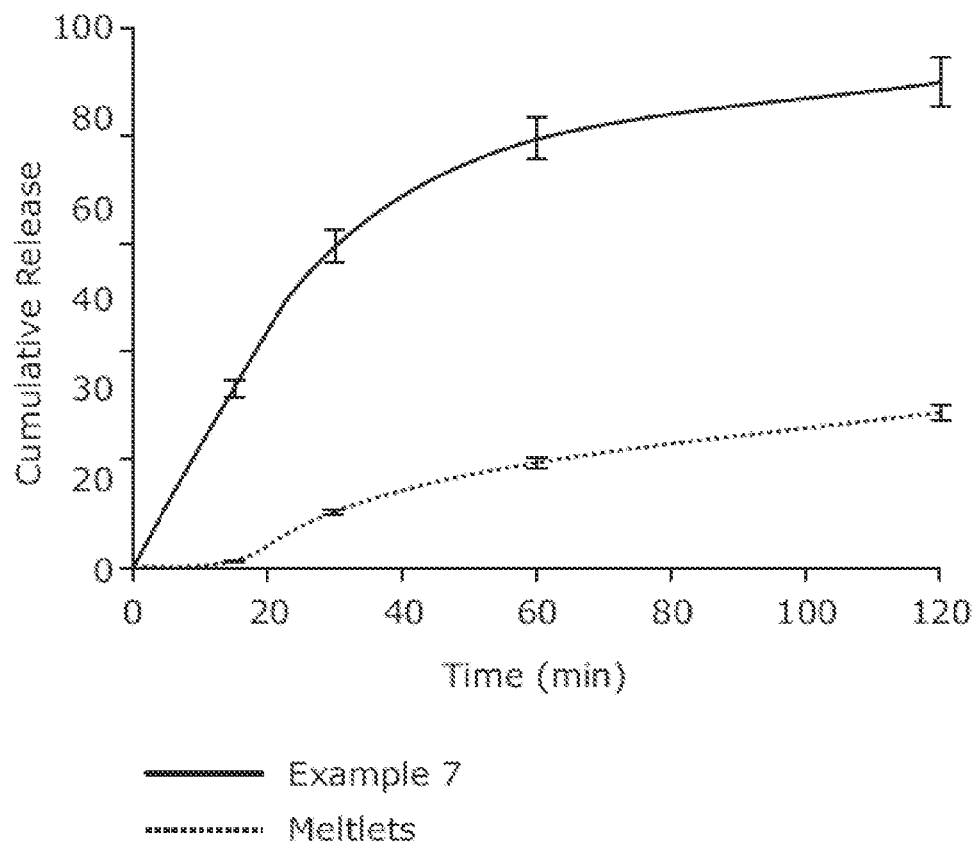
FIG. 5 shows the results of a dissolution test conducted to compare the dissolution rates of Example 7 of the present invention and a commercially available "Mallets" product.

FIG. 5 shows the results from these studies for Example 7, vs. the results for the commercial Nurofen Meltlet product. In FIG. 5, the top graph line represents the results from Example 7 the bottom graph line represents the results from the Nurofen Meltlet product. It can be seen that the dissolution rate for the poorly water-soluble ibuprofen has been considerably increased (by a factor of about 3) compared to that seen in the Meltlet product.

The present invention also provides improved bioavailability of ibuprofen compared to pure ibuprofen. This was tested as described below.

Figure 6:
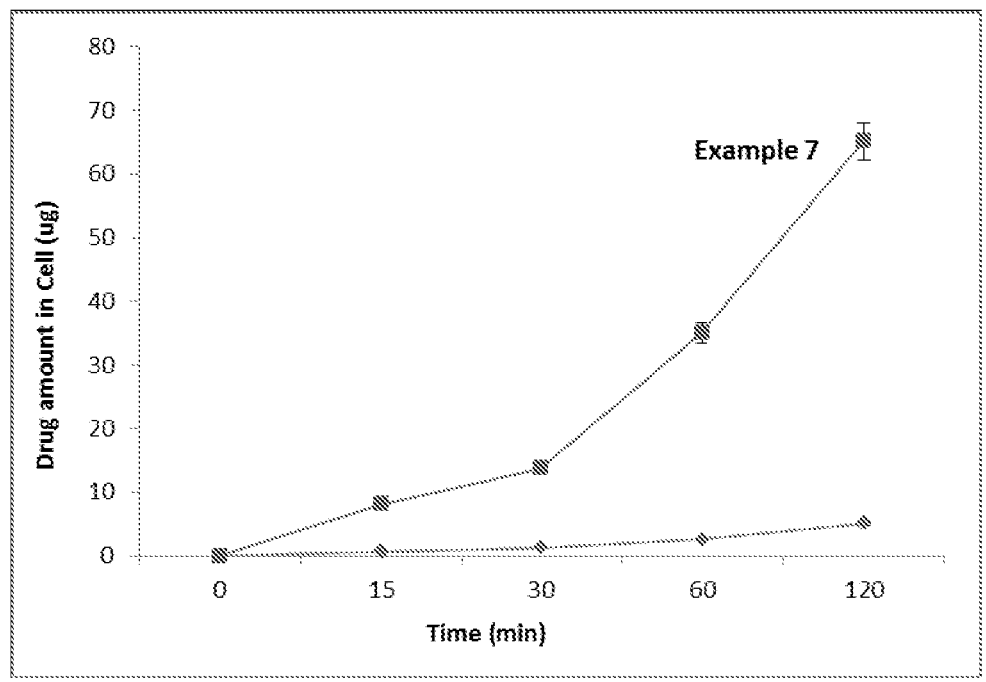
FIG. 6 shows the results of an in vitro bioavailability study conducted to compare the bioavailability of Example 7 and pure ibuprofen.

Method: In vitro bioavailability of IBU was determined using Caco-2 cell culture. Caco-2 cells were grown at 37° C., 5% $CO_2$ and 95% relative humidity using Dulbecco's Modified Essential Medium (MEM) supplemented with 10% fatal bovine serum, 1% non-essential amino acids, and 0.05% penicillin/streptomycin/amphotericin. Cells were passaged at 80-90% confluency using a 0.25% trypsin/ 0.20% ethylene diamine tetraacetic acid (EDTA) solution. Media was changed approximately every 24 h. Caco-2 cells (passages 48-60) were seeded at $6.5 \times 10^4$ cells/cm$^2$ on polycarbonate 10×6-well plates (Corning Costar Corporation, Cambridge, MA) (3.0 μm mean pore size) and used for transport experiments 14 days after seeding. In order to determine the permeability, Caco-2 cell monolayers were incubated at 37° C., 5% CO2 and 95% relative humidity while shaking at 100 RPM and samples were collected from the receiver compartment after 15, 30, 60 and 120 min. Permeability of IBU across Caco-2 cell monolayers (Pm) was estimated by correcting the effective permeability ($P_{eff}$) for filter permeability ($P_{filter}$) according to: $P_{eff}^{-1}=P_m^{-1}+P_{filter}^{-1}$ equation. The results are shown in FIG. 6. FIG. 6 shows that in vitro Caco-2 cell culture studies showed 12 fold increase of ibuprofen bioavailability in the formulation of Example 7 compared to bulk (pure) ibuprofen.

The invention claimed is:

1. A method of producing a direct compression tablet comprising ibuprofen, said method comprising the steps of:
   (a) providing ibuprofen;
   (b) providing a hydrophilic polymer selected from the group consisting of i) copolymers based on dimethylaminoethyl methacrylate, butyl methacrylate and methyl methacrylate; and ii) N-vinyl-2-pyrrolidone and vinyl acetate copolymers;
   (c) providing an inorganic excipient, wherein the inorganic excipient is a metal aluminosilicate;
   (d) processing (a) to (c) by a hot melt extrusion process to produce an extruded composition wherein the hydrophilic polymer is provided in an amount sufficient for at least 90 wt %, 95 wt %, or 98 wt % of the ibuprofen to form a solid amorphous dispersion/solution within the hydrophilic polymer, and wherein the metal aluminosilicate is provided in an amount greater than or equal to 10 wt % based on the weight of the extruded composition;
   e) blending the extruded composition with one or more pharmaceutically acceptable excipients to produce a composition blend; and
   (f) directly compressing the composition blend into an orally-disintegrating tablet.

2. The method according to claim 1 wherein the extruded composition comprises less than or equal to 60 wt % ibuprofen.

3. The method according to claim 1 wherein the extruded composition is in the form of a strand.

4. The method according to claim 1, further comprising cutting the extruded composition into pellets.

5. The method according to claim 4 further comprising micronization of the pellets.

6. The method according to claim 1 wherein the inorganic excipient has a specific surface area of more than 200 m$^2$/g.

7. The method according to claim 1 wherein the inorganic excipient has a Carr Index of less than 18.

8. The method according to claim 1 wherein the metal aluminosilicate is provided in an amount greater than or equal to 15 wt % based on the weight of the extruded composition.

9. The method according to claim 1 wherein the inorganic excipient is magnesium alumino-metasilicate ($Al_2O_3 \cdot MgO \cdot 1.7SiO_2 \cdot xH_2O$).

10. A direct compression tablet composition obtainable by a method as defined in claim 1.

11. A method according to claim 1 wherein the metal aluminosilicate is provided in an amount greater than or equal to 20 wt % based on the weight of the extruded composition.

12. A method according to claim 1, wherein at least 90% w/w of the ibuprofen in the extruded composition is in the form of a solid dispersion/solution.

13. A method according to claim 1, wherein at least 95% w/w of the ibuprofen in the extruded composition is in the form of a solid dispersion/solution.

14. A method according to claim 1 wherein a degree of crystallinity of the extruded composition is less than 15%.

15. A method according to claim 1 wherein a degree of crystallinity of the extruded composition is less than 5%.

16. A method of producing a direct compression tablet comprising ibuprofen, said method comprising the steps of:
(a) providing ibuprofen;
(b) providing a hydrophilic polymer selected from the group consisting of:
i) copolymers based on dimethylaminoethyl methacrylate, butyl methacrylate and methyl methacrylate in an amount of 15 wt % to 40 wt %; and ii) N-vinyl-2-pyrrolidone and vinyl acetate copolymers in an amount of 30 wt % to 35 wt;
(c) providing an inorganic excipient, wherein the inorganic excipient is a metal aluminosilicate;
(d) processing (a) to (c) by a hot melt extrusion process to produce an extruded composition wherein the ibuprofen forms a solid amorphous dispersion/solution within the hydrophilic polymer, and wherein the metal aluminosilicate is provided in an amount greater than or equal to 10 wt % based on the weight of the extruded composition;
(e) blending the extruded composition with one or more pharmaceutically acceptable excipients to produce a composition blend; and
(f) directly compressing the composition blend into an orally-disintegrating tablet.

17. A method according to claim 1, wherein the metal aluminosilicate is provided in an amount of up to 45 wt % based on the weight of the extruded composition.

* * * * *